United States Patent
Terrill et al.

(10) Patent No.: US 10,238,382 B2
(45) Date of Patent: Mar. 26, 2019

(54) BLADE ANCHOR FOR FOOT AND ANKLE

(71) Applicant: Hyun Bae, Santa Monica, CA (US)

(72) Inventors: Lance N. Terrill, Oviedo, FL (US); Michael Chad Hollis, Collierville, TN (US)

(73) Assignee: Engage Medical Holdings, LLC, Los Angeles, CA (US)

( * ) Notice: Subject to any disclaimer, the term of this patent is extended or adjusted under 35 U.S.C. 154(b) by 0 days.

(21) Appl. No.: 13/851,024

(22) Filed: Mar. 26, 2013

(65) Prior Publication Data
US 2013/0267956 A1 Oct. 10, 2013

Related U.S. Application Data (60) Provisional application No. 61/615,773, filed on Mar. 26, 2012.

(51) Int. Cl.
*A61B 17/56* (2006.01)
*A61B 17/064* (2006.01)
*A61B 17/68* (2006.01)

(52) U.S. Cl.
CPC .......... *A61B 17/0642* (2013.01); *A61B 17/68* (2013.01)

(58) Field of Classification Search
CPC .............. A61B 17/064; A61B 17/0642; A61B 17/0643; A61B 17/0644; A61B 2017/0641; A61B 2017/0645; A61B 2017/0646; A61B 2017/0649; A61B 17/68; Y10T 24/49; Y10T 24/492; Y10T 24/497

USPC .................. 606/75, 138, 219; 227/901–902, 227/175.1–182.1
See application file for complete search history.

(56) References Cited

U.S. PATENT DOCUMENTS

| | | |
|---|---|---|
| 3,486,505 A | 12/1969 | Morrison |
| 3,641,590 A | 2/1972 | Michele |
| 3,650,309 A | 3/1972 | Neuschotz |
| 3,842,825 A | 10/1974 | Wagner |
| 3,848,276 A | 11/1974 | Martinez |
| 3,882,917 A | 5/1975 | Orlomoski |
| 3,896,504 A | 7/1975 | Fischer |
| 3,907,017 A | 9/1975 | Stanwick |
| 3,927,503 A | 12/1975 | Wilson |
| 4,011,602 A | 3/1977 | Rybicki |
| 4,047,524 A | 9/1977 | Hall |
| 4,260,005 A | 4/1981 | Stencel |
| 4,349,955 A | 9/1982 | Keen |
| 4,355,429 A | 10/1982 | Mittelmeier |
| 4,454,875 A * | 6/1984 | Pratt ........................ F16B 15/02 606/219 |
| 4,484,570 A | 11/1984 | Sutter |

(Continued)

FOREIGN PATENT DOCUMENTS

| | | |
|---|---|---|
| EP | 179695 A1 | 4/1986 |
| EP | 1327423 | 7/2003 |

(Continued)

*Primary Examiner* — Zade Coley
*Assistant Examiner* — Jessica Weiss
(74) *Attorney, Agent, or Firm* — Maywood IP Law; Stuart S. Bray; David Meibos (57) ABSTRACT

Fixation devices for the foot and ankle are based on a design with a central portion between a pair of blade anchors. The central portion may include sharpening, apertures, notches, or protrusions. The fixation devices may engage two or more bone portions.

17 Claims, 10 Drawing Sheets

(56) References Cited

U.S. PATENT DOCUMENTS

| | | | |
|---|---|---|---|
| 4,501,269 A | 2/1985 | Bagby | |
| D281,814 S * | 12/1985 | Pratt | D24/145 |
| 4,570,623 A * | 2/1986 | Ellison | A61B 17/0642 606/75 |
| 4,611,581 A | 9/1986 | Steffee | |
| 4,642,869 A | 2/1987 | Muller | |
| 4,681,589 A | 7/1987 | Tronzo | |
| 4,716,893 A | 1/1988 | Fischer | |
| 4,743,256 A | 5/1988 | Brantigan | |
| 4,743,262 A | 5/1988 | Tronzo | |
| 4,764,067 A | 8/1988 | Kawashima | |
| 4,820,305 A | 4/1989 | Harms | |
| 4,834,757 A | 5/1989 | Brantigan | |
| 4,838,891 A | 6/1989 | Branemark | |
| 4,848,328 A * | 7/1989 | Laboureau | A61B 17/0642 606/75 |
| 4,865,607 A | 9/1989 | Witzel | |
| 4,874,389 A | 10/1989 | Downey | |
| 4,930,962 A | 6/1990 | Reynolds | |
| 4,946,378 A | 8/1990 | Hirayama | |
| 4,957,496 A | 9/1990 | Schmidt | |
| 5,002,576 A | 3/1991 | Fuhrmann | |
| 5,019,103 A | 5/1991 | Van Zile | |
| 5,053,038 A * | 10/1991 | Sheehan | A61B 17/0642 606/75 |
| 5,074,880 A | 12/1991 | Mansat | |
| 5,147,361 A | 9/1992 | Ojima | |
| 5,163,960 A | 11/1992 | Bonutti | |
| 5,192,324 A | 3/1993 | Kenna | |
| 5,192,327 A | 3/1993 | Brantigan | |
| 5,306,309 A | 4/1994 | Wagner | |
| 5,314,477 A | 5/1994 | Marnay | |
| 5,352,229 A * | 10/1994 | Goble | A61B 17/0642 606/220 |
| 5,366,479 A * | 11/1994 | McGarry | A61B 17/0684 227/902 |
| 5,431,658 A | 7/1995 | Moskovich | |
| 5,443,515 A | 8/1995 | Cohen | |
| 5,449,359 A | 9/1995 | Groiso | |
| 5,454,814 A * | 10/1995 | Comte | A61B 17/0642 606/219 |
| D364,462 S | 11/1995 | Michelson | |
| 5,507,816 A | 4/1996 | Bullivant | |
| 5,514,180 A | 5/1996 | Heggeness | |
| D378,409 S | 3/1997 | Michelson | |
| 5,609,635 A | 3/1997 | Michelson | |
| 5,658,337 A | 8/1997 | Kohrs | |
| 5,660,188 A | 8/1997 | Groiso | |
| 5,683,394 A | 11/1997 | Rinner | |
| 5,702,449 A | 12/1997 | McKay | |
| 5,709,683 A | 1/1998 | Bagby | |
| 5,713,899 A | 2/1998 | Marnay | |
| 5,769,852 A | 6/1998 | Branemark | |
| 5,772,661 A | 6/1998 | Michelson | |
| 5,776,199 A | 7/1998 | Michelson | |
| 5,776,202 A | 7/1998 | Copf | |
| 5,788,701 A | 8/1998 | McCue | |
| 5,800,550 A | 9/1998 | Sertich | |
| 5,853,414 A | 12/1998 | Groiso | |
| 5,860,973 A | 1/1999 | Michelson | |
| 5,885,287 A | 3/1999 | Bagby | |
| 5,893,889 A | 4/1999 | Harrington | |
| 5,893,890 A | 4/1999 | Pisharodi | |
| 5,947,999 A | 9/1999 | Groiso | |
| 5,993,476 A | 11/1999 | Groiso | |
| 6,039,762 A | 3/2000 | McKay | |
| 6,059,787 A * | 5/2000 | Allen | A61B 17/0642 606/75 |
| 6,063,121 A | 5/2000 | Xavier | |
| 6,080,155 A | 6/2000 | Michelson | |
| 6,096,080 A | 8/2000 | Nicholson | |
| 6,102,949 A | 8/2000 | Biedermann | |
| 6,113,638 A | 9/2000 | Williams | |
| 6,120,503 A | 9/2000 | Michelson | |
| 6,136,001 A | 10/2000 | Michelson | |
| 6,159,214 A | 12/2000 | Michelson | |
| 6,224,607 B1 | 5/2001 | Michelson | |
| 6,235,059 B1 | 5/2001 | Benezech | |
| 6,241,769 B1 | 6/2001 | Nicholson | |
| 6,241,770 B1 | 6/2001 | Michelson | |
| 6,270,498 B1 | 8/2001 | Michelson | |
| 6,302,914 B1 | 10/2001 | Michelson | |
| 6,309,421 B1 | 10/2001 | Pisharodi | |
| 6,325,805 B1 * | 12/2001 | Ogilvie | A61B 17/0642 606/300 |
| 6,336,928 B1 | 1/2002 | Guerin | |
| 6,364,880 B1 | 4/2002 | Michelson | |
| 6,402,785 B1 | 6/2002 | Zdeblick | |
| 6,413,278 B1 | 7/2002 | Marchosky | |
| 6,432,107 B1 | 8/2002 | Ferree | |
| 6,436,098 B1 | 8/2002 | Michelson | |
| 6,447,524 B1 | 9/2002 | Knodel | |
| 6,447,544 B1 | 9/2002 | Michelson | |
| 6,447,546 B1 | 9/2002 | Bramlet | |
| 6,458,159 B1 | 10/2002 | Thalgott | |
| 6,478,800 B1 | 11/2002 | Fraser | |
| 6,485,517 B1 | 11/2002 | Michelson | |
| 6,506,216 B1 | 1/2003 | McCue | |
| 6,558,424 B2 | 2/2003 | Thalgott | |
| 6,537,320 B1 | 3/2003 | Michelson | |
| 6,558,423 B1 | 5/2003 | Michelson | |
| 6,582,468 B1 | 6/2003 | Gauchet | |
| 6,599,294 B2 | 7/2003 | Fuss | |
| 6,610,093 B1 | 8/2003 | Pisharodi | |
| 6,620,198 B2 | 9/2003 | Burstein | |
| 6,652,533 B2 | 11/2003 | O'Neil | |
| 6,679,887 B2 | 1/2004 | Nicholson | |
| 6,716,245 B2 | 4/2004 | Pasquet | |
| 6,726,720 B2 | 4/2004 | Ross | |
| 6,740,118 B2 | 5/2004 | Eisermann | |
| 6,743,256 B2 | 6/2004 | Mason | |
| 6,746,450 B1 | 6/2004 | Wall | |
| 6,755,841 B2 | 6/2004 | Fraser | |
| 6,767,356 B2 * | 7/2004 | Kanner | A61B 17/0057 227/175.1 |
| 6,767,367 B1 | 7/2004 | Michelson | |
| 6,770,074 B2 | 8/2004 | Michelson | |
| 6,770,096 B2 | 8/2004 | Bolger | |
| 6,773,437 B2 | 8/2004 | Ogilvie | |
| 6,800,093 B2 | 10/2004 | Nicholson | |
| 6,802,863 B2 | 10/2004 | Lawson | |
| 6,827,740 B1 | 12/2004 | Michelson | |
| 6,835,208 B2 | 12/2004 | Marchosky | |
| 6,849,093 B2 | 2/2005 | Michelson | |
| 6,875,213 B2 | 4/2005 | Michelson | |
| 6,923,810 B1 | 8/2005 | Michelson | |
| 6,923,830 B2 | 8/2005 | Michelson | |
| 6,926,718 B1 | 8/2005 | Michelson | |
| 6,942,698 B1 | 9/2005 | Jackson | |
| 6,969,390 B2 | 11/2005 | Michelson | |
| 6,972,035 B2 | 12/2005 | Michelson | |
| 6,981,975 B2 | 1/2006 | Michelson | |
| 6,989,031 B2 | 1/2006 | Michelson | |
| 7,033,394 B2 | 4/2006 | Michelson | |
| 7,041,135 B2 | 5/2006 | Michelson | |
| 7,044,972 B2 | 5/2006 | Mathys, Jr. | |
| 7,048,766 B2 | 5/2006 | Ferree | |
| 7,056,344 B2 | 6/2006 | Huppert | |
| 7,056,345 B2 | 6/2006 | Kuslich | |
| 7,060,097 B2 | 6/2006 | Fraser | |
| 7,066,961 B2 | 6/2006 | Michelson | |
| 7,083,623 B2 | 8/2006 | Michelson | |
| 7,083,652 B2 | 8/2006 | McCue | |
| 7,087,082 B2 | 8/2006 | Paul | |
| 7,112,206 B2 | 9/2006 | Michelson | |
| 7,115,146 B2 | 10/2006 | Boyer, II | |
| 7,118,580 B1 | 10/2006 | Beyersdorff | |
| 7,128,761 B2 | 10/2006 | Kuras | |
| 7,163,560 B2 | 1/2007 | Mason | |
| 7,166,110 B2 | 1/2007 | Yundt | |
| 7,166,129 B2 | 1/2007 | Michelson | |
| 7,169,182 B2 | 1/2007 | Errico | |
| 7,204,852 B2 | 4/2007 | Marnay | |

(56) References Cited

U.S. PATENT DOCUMENTS

| | | |
|---|---|---|
| 7,235,101 B2 | 6/2007 | Berry |
| 7,235,105 B2 | 6/2007 | Jackson |
| 7,255,698 B2 | 8/2007 | Michelson |
| 7,320,707 B2 | 1/2008 | Zucherman |
| 7,326,248 B2 | 2/2008 | Michelson |
| 7,331,995 B2 | 2/2008 | Eisermann |
| 7,357,817 B2 | 4/2008 | D'Alessio, II |
| 7,364,589 B2 | 4/2008 | Eisermann |
| 7,396,365 B2 | 7/2008 | Michelson |
| 7,462,196 B2 | 12/2008 | Fraser |
| 7,481,830 B2 | 1/2009 | Wall |
| 7,481,832 B1 * | 1/2009 | Meridew ............ A61B 17/0401 606/232 |
| D586,915 S * | 2/2009 | Grim ............................ D24/145 |
| 7,491,205 B1 | 2/2009 | Michelson |
| 7,503,933 B2 | 3/2009 | Michelson |
| 7,503,934 B2 | 3/2009 | Eisermann |
| 7,503,935 B2 | 3/2009 | Zucherman |
| D594,986 S | 6/2009 | Miles |
| 7,540,882 B2 | 6/2009 | Michelson |
| 7,556,650 B2 | 7/2009 | Collins |
| 7,572,293 B2 | 8/2009 | Rhodes |
| 7,588,600 B2 | 9/2009 | Benzel |
| 7,594,931 B2 | 9/2009 | Louis |
| 7,611,538 B2 | 11/2009 | Belliard |
| 7,658,766 B2 | 2/2010 | Melkent |
| 7,695,516 B2 | 4/2010 | Zeegers |
| 7,749,271 B2 | 7/2010 | Fischer |
| 7,763,076 B2 | 7/2010 | Navarro |
| 7,780,676 B2 | 8/2010 | Lakin |
| 7,837,732 B2 | 11/2010 | Zucherman |
| 7,850,791 B2 * | 12/2010 | Quadakkers ............ C23C 2/26 148/240 |
| 7,883,510 B2 * | 2/2011 | Kim .................... A61B 17/0642 606/75 |
| 7,887,563 B2 * | 2/2011 | Cummins .......... A61B 17/0644 606/213 |
| 7,896,919 B2 | 3/2011 | Belliard |
| 7,909,871 B2 | 3/2011 | Abdou |
| 7,918,891 B1 | 4/2011 | Curran |
| 7,966,799 B2 * | 6/2011 | Morgan ............. A61B 17/0644 411/469 |
| 8,021,403 B2 | 9/2011 | Wall |
| 8,034,076 B2 | 10/2011 | Criscuolo |
| 8,100,972 B1 | 1/2012 | Bruffey |
| 8,100,974 B2 | 1/2012 | Duggal |
| 8,105,389 B2 | 1/2012 | Berelsman |
| 8,123,757 B2 | 2/2012 | Zalenski |
| 8,133,283 B2 | 3/2012 | Wilson |
| 8,157,865 B2 | 4/2012 | Hochschuler |
| 8,491,598 B2 | 7/2013 | Crook |
| 8,500,747 B2 | 8/2013 | DeRidder |
| 8,636,191 B2 * | 1/2014 | Meagher ............ A61B 17/0644 227/179.1 |
| 8,747,412 B2 | 6/2014 | Bae |
| 8,808,294 B2 * | 8/2014 | Fox .................... A61B 17/0642 606/75 |
| 9,254,130 B2 | 2/2016 | Hollis |
| 9,480,511 B2 | 11/2016 | Butters |
| 2001/0000532 A1 | 4/2001 | Michelson |
| 2001/0010001 A1 | 7/2001 | Michelson |
| 2001/0010002 A1 | 7/2001 | Michelson |
| 2001/0010020 A1 | 7/2001 | Michelson |
| 2001/0037154 A1 | 11/2001 | Martin |
| 2001/0047207 A1 | 11/2001 | Michelson |
| 2001/0047208 A1 | 11/2001 | Michelson |
| 2002/0004683 A1 | 1/2002 | Michelson |
| 2002/0013624 A1 | 1/2002 | Michelson |
| 2002/0035400 A1 | 3/2002 | Bryan |
| 2002/0049447 A1 | 4/2002 | Li |
| 2002/0091390 A1 | 7/2002 | Michelson |
| 2002/0091392 A1 | 7/2002 | Michelson |
| 2002/0095155 A1 | 7/2002 | Michelson |
| 2002/0099376 A1 | 7/2002 | Michelson |
| 2002/0099378 A1 | 7/2002 | Michelson |
| 2002/0116065 A1 | 8/2002 | Jackson |
| 2002/0116165 A1 | 8/2002 | El-Ghoroury |
| 2002/0147454 A1 | 10/2002 | Neto |
| 2002/0147499 A1 | 10/2002 | Shea |
| 2002/0161443 A1 | 10/2002 | Michelson |
| 2002/0165613 A1 | 11/2002 | Lin |
| 2003/0023307 A1 | 1/2003 | Michelson |
| 2003/0040798 A1 | 2/2003 | Michelson |
| 2003/0045940 A1 | 3/2003 | Eberlein |
| 2003/0060884 A1 | 3/2003 | Fell |
| 2003/0100949 A1 | 5/2003 | Michelson |
| 2003/0120344 A1 | 6/2003 | Michelson |
| 2003/0149483 A1 | 8/2003 | Michelson |
| 2003/0158553 A1 | 8/2003 | Michelson |
| 2003/0195517 A1 | 10/2003 | Michelson |
| 2003/0195561 A1 * | 10/2003 | Carley ............... A61B 17/0057 606/213 |
| 2003/0195632 A1 | 10/2003 | Foley |
| 2004/0030336 A1 | 2/2004 | Khanna |
| 2004/0030339 A1 | 2/2004 | Wack |
| 2004/0034353 A1 | 2/2004 | Michelson |
| 2004/0064185 A1 | 4/2004 | Michelson |
| 2004/0073315 A1 | 4/2004 | Justin |
| 2004/0083005 A1 | 4/2004 | Jacobsson |
| 2004/0117018 A1 | 6/2004 | Michelson |
| 2004/0122518 A1 | 6/2004 | Rhoda |
| 2004/0133203 A1 | 7/2004 | Young |
| 2004/0148028 A1 | 7/2004 | Ferree |
| 2004/0176853 A1 | 9/2004 | Sennett |
| 2004/0193271 A1 | 9/2004 | Fraser |
| 2004/0199254 A1 | 10/2004 | Louis |
| 2004/0210313 A1 | 10/2004 | Michelson |
| 2004/0210314 A1 | 10/2004 | Michelson |
| 2004/0215203 A1 | 10/2004 | Michelson |
| 2004/0220668 A1 | 11/2004 | Eisermann |
| 2004/0220670 A1 | 11/2004 | Eisermann |
| 2004/0225295 A1 | 11/2004 | Zubok |
| 2004/0225365 A1 | 11/2004 | Eisermann |
| 2004/0230308 A1 | 11/2004 | Michelson |
| 2004/0249388 A1 | 12/2004 | Michelson |
| 2004/0254581 A1 | 12/2004 | Leclair |
| 2004/0254644 A1 | 12/2004 | Taylor |
| 2004/0260286 A1 | 12/2004 | Ferree |
| 2005/0004672 A1 | 1/2005 | Pafford |
| 2005/0014919 A1 | 1/2005 | Hatakeyama |
| 2005/0027300 A1 | 2/2005 | Hawkins |
| 2005/0038512 A1 | 2/2005 | Michelson |
| 2005/0038513 A1 | 2/2005 | Michelson |
| 2005/0043802 A1 | 2/2005 | Eisermann |
| 2005/0049600 A1 | 3/2005 | Groiso |
| 2005/0055031 A1 | 3/2005 | Lim |
| 2005/0125065 A1 | 6/2005 | Zucherman |
| 2005/0131545 A1 | 6/2005 | Chervitz |
| 2005/0143747 A1 | 6/2005 | Zubok |
| 2005/0149192 A1 | 7/2005 | Zucherman |
| 2005/0149193 A1 | 7/2005 | Zucherman |
| 2005/0165408 A1 | 7/2005 | Puno |
| 2005/0171606 A1 | 8/2005 | Michelson |
| 2005/0171607 A1 | 8/2005 | Michelson |
| 2005/0177239 A1 | 8/2005 | Steinberg |
| 2005/0187628 A1 | 8/2005 | Michelson |
| 2005/0187629 A1 | 8/2005 | Michelson |
| 2005/0192586 A1 | 9/2005 | Zucherman |
| 2005/0216083 A1 | 9/2005 | Michelson |
| 2005/0216089 A1 | 9/2005 | Michelson |
| 2005/0234555 A1 | 10/2005 | Sutton |
| 2005/0273108 A1 | 12/2005 | Groiso |
| 2005/0277933 A1 | 12/2005 | Wall |
| 2006/0004453 A1 | 1/2006 | Bartish |
| 2006/0058802 A1 * | 3/2006 | Kofoed ............... A61B 17/0642 606/75 |
| 2006/0074421 A1 | 4/2006 | Bickley |
| 2006/0079961 A1 | 4/2006 | Michelson |
| 2006/0085071 A1 | 4/2006 | Lechmann |
| 2006/0095136 A1 | 5/2006 | McLuen |
| 2006/0111787 A1 | 5/2006 | Bailie |
| 2006/0116769 A1 | 6/2006 | Marnay |
| 2006/0122702 A1 | 6/2006 | Michelson |

(56) References Cited

U.S. PATENT DOCUMENTS

| | | |
|---|---|---|
| 2006/0129238 A1 | 6/2006 | Paltzer |
| 2006/0136061 A1 | 6/2006 | Navarro |
| 2006/0136063 A1 | 6/2006 | Zeegers |
| 2006/0142860 A1 | 6/2006 | Navarro |
| 2006/0149377 A1 | 7/2006 | Navarro |
| 2006/0149384 A1 | 7/2006 | Navarro |
| 2006/0167461 A1 | 7/2006 | Hawkins |
| 2006/0178745 A1 | 8/2006 | Bartish |
| 2006/0195097 A1 | 8/2006 | Evans |
| 2006/0212123 A1 | 9/2006 | Lechmann |
| 2006/0241641 A1 | 10/2006 | Albans |
| 2006/0259143 A1 | 11/2006 | Navarro |
| 2006/0259145 A1 | 11/2006 | Navarro |
| 2006/0259146 A1 | 11/2006 | Navarro |
| 2007/0010890 A1 | 1/2007 | Collazo |
| 2007/0050032 A1 | 3/2007 | Gittings |
| 2007/0055376 A1 | 3/2007 | Michelson |
| 2007/0066981 A1* | 3/2007 | Meagher ............ A61B 17/0644 606/153 |
| 2007/0073404 A1 | 3/2007 | Rashbaum |
| 2007/0093839 A1* | 4/2007 | Beckendorf ....... A61B 17/0642 606/75 |
| 2007/0106388 A1 | 5/2007 | Michelson |
| 2007/0118132 A1 | 5/2007 | Culbert |
| 2007/0118145 A1 | 5/2007 | Fischer |
| 2007/0123903 A1 | 5/2007 | Raymond |
| 2007/0142922 A1 | 6/2007 | Lewis |
| 2007/0185375 A1 | 8/2007 | Stad |
| 2007/0191850 A1* | 8/2007 | Kim et al. ....................... 606/75 |
| 2007/0233244 A1 | 10/2007 | Lopez |
| 2007/0239278 A1 | 10/2007 | Heinz |
| 2007/0288005 A1 | 12/2007 | Arnin |
| 2007/0288021 A1 | 12/2007 | Rickels |
| 2007/0299529 A1 | 12/2007 | Rhodes |
| 2008/0015702 A1 | 1/2008 | Lakin |
| 2008/0051901 A1 | 2/2008 | De Villiers |
| 2008/0051902 A1 | 2/2008 | Dwyer |
| 2008/0103598 A1 | 5/2008 | Trudeau |
| 2008/0108997 A1* | 5/2008 | Berrevoets ......... A61B 17/7044 606/251 |
| 2008/0132949 A1 | 6/2008 | Aferzon |
| 2008/0140208 A1 | 6/2008 | Zucherman |
| 2008/0147203 A1 | 6/2008 | Cronin |
| 2008/0154377 A1 | 6/2008 | Voellmicke |
| 2008/0167721 A1 | 7/2008 | Bao |
| 2008/0177275 A1 | 7/2008 | Wing |
| 2008/0208345 A1 | 8/2008 | Hurlbert |
| 2008/0249575 A1 | 10/2008 | Waugh |
| 2008/0249623 A1 | 10/2008 | Bao |
| 2008/0269764 A1 | 10/2008 | Blain |
| 2008/0275455 A1 | 11/2008 | Berry |
| 2008/0287957 A1 | 11/2008 | Hester |
| 2009/0005784 A1 | 1/2009 | Blain |
| 2009/0005870 A1 | 1/2009 | Hawkins |
| 2009/0048604 A1 | 2/2009 | Milz |
| 2009/0062921 A1 | 3/2009 | Michelson |
| 2009/0088849 A1 | 4/2009 | Armstrong |
| 2009/0099601 A1 | 4/2009 | Aferzon |
| 2009/0099602 A1 | 4/2009 | Aflatoon |
| 2009/0164020 A1 | 6/2009 | Janowski |
| 2009/0209967 A1 | 8/2009 | Evans |
| 2009/0240333 A1 | 9/2009 | Trudeau |
| 2010/0004747 A1 | 1/2010 | Lin |
| 2010/0023062 A1* | 1/2010 | Faillace ............. A61B 17/0642 606/297 |
| 2010/0069958 A1 | 3/2010 | Sullivan |
| 2010/0185287 A1 | 7/2010 | Allard |
| 2010/0185292 A1 | 7/2010 | Hochschuler |
| 2010/0201739 A1 | 8/2010 | Yamaguchi |
| 2010/0204737 A1 | 8/2010 | Bae |
| 2010/0204739 A1 | 8/2010 | Bae |
| 2011/0022176 A1 | 1/2011 | Zucherman |
| 2011/0098819 A1 | 4/2011 | Eisermann |
| 2011/0160766 A1* | 6/2011 | Hendren ............ A61B 17/0487 606/232 |
| 2011/0160866 A1 | 6/2011 | Laurence |
| 2011/0166608 A1 | 7/2011 | Duggal |
| 2012/0191204 A1 | 7/2012 | Bae |
| 2012/0215315 A1 | 8/2012 | Hochschuler |
| 2012/0239098 A1 | 9/2012 | Bae |
| 2012/0253406 A1 | 10/2012 | Bae |
| 2012/0265259 A1 | 10/2012 | LaPosta |
| 2012/0283837 A1 | 11/2012 | Bae |
| 2013/0013006 A1 | 1/2013 | Rashbaum |
| 2013/0123863 A1* | 5/2013 | Hollis ................ A61B 17/0642 606/328 |
| 2013/0190827 A1 | 7/2013 | Butters |
| 2014/0039632 A1 | 2/2014 | Hollis |
| 2016/0157906 A1 | 6/2016 | Hollis |
| 2017/0042576 A1 | 2/2017 | Butters |

FOREIGN PATENT DOCUMENTS

| | | |
|---|---|---|
| EP | 1790298 | 5/2007 |
| EP | 1827318 | 9/2007 |
| EP | 1872746 | 1/2008 |
| EP | 1897517 | 3/2008 |
| EP | 1983941 | 10/2008 |
| EP | 2651341 | 10/2013 |
| EP | 2685938 | 8/2015 |
| EP | 3178448 | 6/2017 |
| WO | WO1993022990 | 11/1993 |
| WO | WO2000025707 | 5/2000 |
| WO | WO2000064360 | 11/2000 |
| WO | WO2001003570 | 1/2001 |
| WO | WO2002003885 | 1/2002 |
| WO | WO2002003895 A1 | 1/2002 |
| WO | WO2002058593 | 8/2002 |
| WO | WO2003005939 A1 | 1/2003 |
| WO | WO2003039400 A2 | 5/2003 |
| WO | WO2003053290 A1 | 7/2003 |
| WO | WO2003065930 | 8/2003 |
| WO | WO2003092507 A2 | 11/2003 |
| WO | WO2004071359 A2 | 8/2004 |
| WO | WO2004080355 A1 | 9/2004 |
| WO | WO2004089240 | 10/2004 |
| WO | WO2004108015 A2 | 12/2004 |
| WO | WO2005051243 A2 | 6/2005 |
| WO | WO2005074841 A1 | 8/2005 |
| WO | WO2006051547 A2 | 5/2006 |
| WO | WO2006074414 A2 | 7/2006 |
| WO | WO2006086494 A2 | 8/2006 |
| WO | WO 2006/122194 * 11/2006 ............ A61B 17/56 |
| WO | WO2006120505 | 11/2006 |
| WO | WO2007028098 A2 | 3/2007 |
| WO | WO2007034310 | 3/2007 |
| WO | WO2007087366 A2 | 8/2007 |
| WO | WO2008014258 A2 | 1/2008 |
| WO | WO2008014453 A2 | 1/2008 |
| WO | WO2008021955 A2 | 2/2008 |
| WO | WO2008034140 | 3/2008 |
| WO | WO2008128367 A1 | 10/2008 |
| WO | WO2009070721 | 6/2009 |
| WO | WO2010039026 | 4/2010 |
| WO | WO2010121002 | 10/2010 |
| WO | WO2011044879 | 4/2011 |
| WO | WO2011090508 A1 | 7/2011 |
| WO | WO2012083205 | 6/2012 |
| WO | WO2012112598 | 8/2012 |

* cited by examiner

BLADE ANCHOR FOR FOOT AND ANKLE

CROSS REFERENCE TO RELATED APPLICATIONS

This application is a non-provisional of:

U.S. Provisional Patent Application No. 61/615,773, filed and entitled.

The above-identified document is herein incorporated by reference in its entirety.

BACKGROUND

The present disclosure relates to devices for fixation of one or more bones of the foot or ankle. The disclosed devices may be used in syndesmotic junctions or midfoot or hindfoot arthrodeses or osteotomies, such as Akin, Weil, Chevron, and others known in the surgical arts. The disclosed devices may also be used in deformity corrections, such as lateral column, bunion, and the like. The disclosed devices may also be used in fracture fixation, such as Jones, LisFrank, fibular fractures, and the like. The disclosed devices may be used in pilon fractures as primary or secondary fixation devices. The disclosed devices may be used to fuse interphalangeal interphalangeal joints in the foot or hand; in these situations, the central portion of the device may be arc shaped to clear the endplates of the metaphysis. The disclosed devices may be applicable as tether devices for epiphyseal fracture repair in skeletally immature patients.

BRIEF DESCRIPTION OF THE DRAWINGS

While examples of the present technology have been shown and described in detail below, it will be clear to the person skilled in the art that variations, changes and modifications may be made without departing from its scope. As such, that which is set forth in the following description and accompanying drawings is offered by way of illustration only and not as a limitation. The actual scope of the invention is intended to be defined by the following claims, along with the full range of equivalents to which such claims are entitled.

In the following Detailed Description, various features are grouped together in several examples for the purpose of streamlining the disclosure. This method of disclosure is not to be interpreted as reflecting an intention that examples of the technology require more features than are expressly recited in each claim. Rather, as the following claims reflect, inventive subject matter lies in less than all features of a single disclosed example. Thus, the following claims are hereby incorporated into the Detailed Description, with each claim standing on its own as a separate example.

Identical reference numerals do not necessarily indicate an identical structure. Rather, the same reference numeral may be used to indicate a similar feature or a feature with similar functionality. Not every feature of each example is labeled in every figure in which that example appears, in order to keep the figures clear. Similar reference numbers (e.g., those that are identical except for the first numeral) are used to indicate similar features in different examples.

DETAILED DESCRIPTION

Standard medical planes of reference and descriptive terminology are employed in this specification. A sagittal plane divides a body into right and left portions. A mid-sagittal plane divides the body into bilaterally symmetric right and left halves. A coronal plane divides a body into anterior and posterior portions. A transverse plane divides a body into superior and inferior portions. Anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body. Ipsilateral means on the same side of the body. Contralateral means on the opposite side of the body. These descriptive terms may be applied to an animate or inanimate body.

The devices disclosed herein may provide fixation between two or more bone portions that relies upon fixation blades rather than screws. Fixation may be desired in situations where temporary or permanent prevention of motion is desired. Fusion is one example of such a situation. Compared to a screw, a fixation blade may conserve more bone, reduce insertion time, reduce inventory, and/or reduce cost. A fixation blade may conserve bone by occupying a smaller volume than a screw, or by having a smaller cross sectional area than the screw in a plane transverse to an axis along which the screw or blade is inserted into the bone. A fixation blade may take less time to insert into bone than a screw. Adequate fixation may be provided by a small set of the devices disclosed herein versus an extensive set of screws of various lengths, diameters, and/or thread forms. A fixation blade may cost less to fabricate and/or inspect than a screw.

The devices disclosed herein may be described as low profile or "no profile" in the sense that these devices may be driven into bone so as to be flush, or level, with the bone surface, or completely submerged within the bone.

The devices disclosed herein may act to compress bone portions together as a result of advancing a device into bone. A secondary compression step may be unnecessary or optional with these devices.

The devices disclosed herein may be arranged or configured for multi-bone or multi-fragment fusions.

The devices disclosed herein may permit visibility of the fixation site(s) due to their low or "no profile" characteristics.

Figure 1:
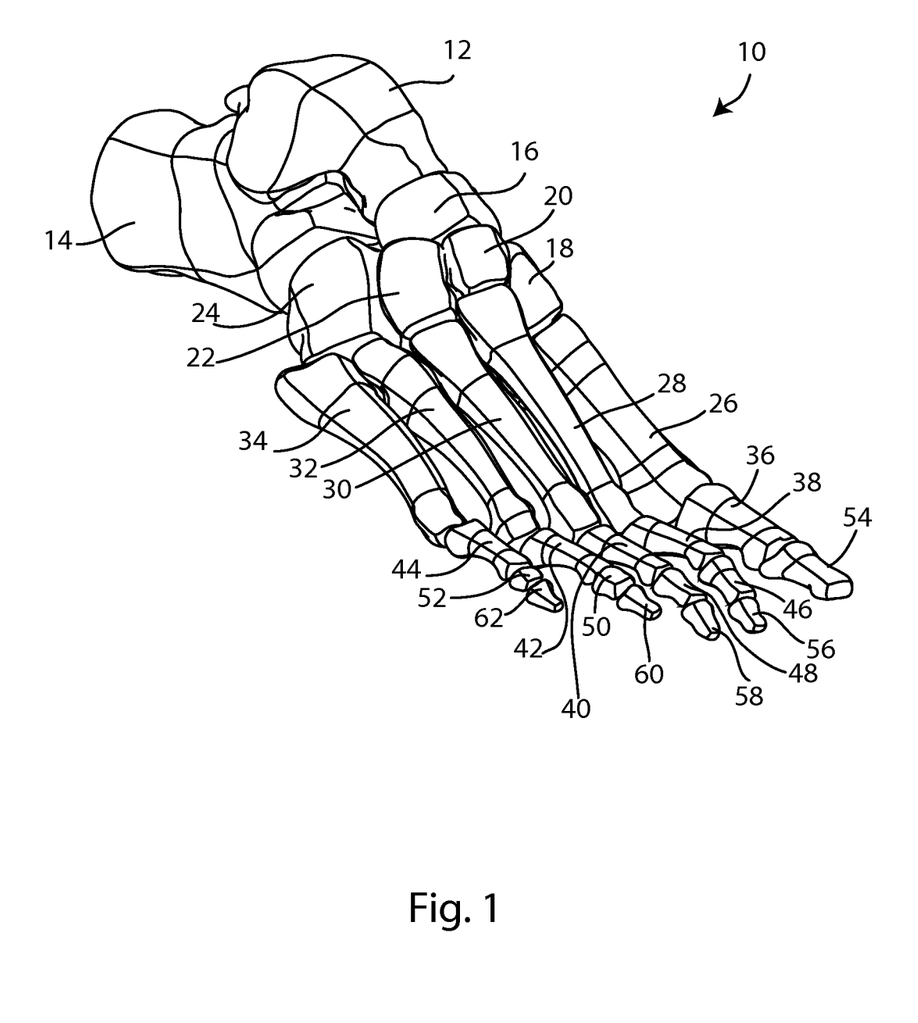
FIG. 1 is a lateral isometric view of a right foot.
Figure 2:
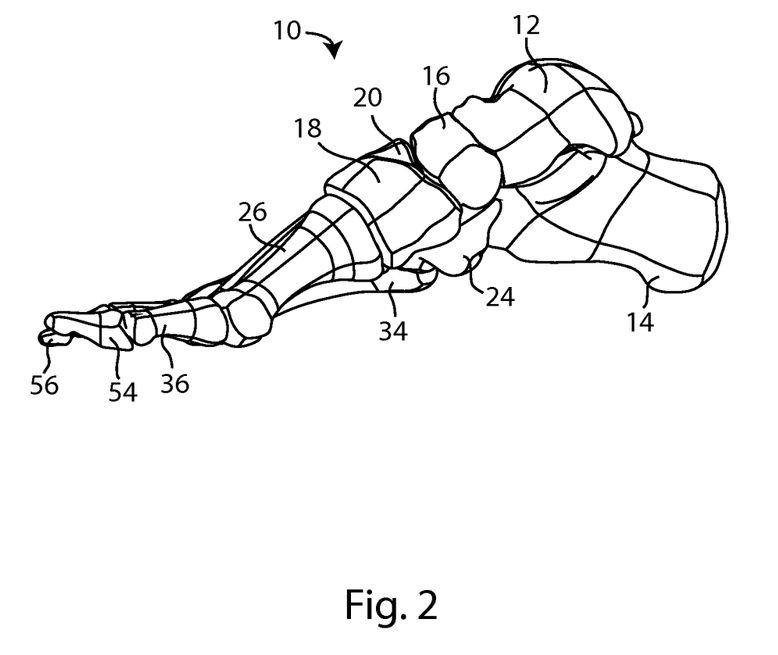
FIG. 2 is a medial isometric view of the right foot of FIG. 1.

Referring to FIGS. 1-2, a normal human foot 10 includes twenty-six bones, including a talus bone 12, a calcaneus bone 14, a navicular bone 16, a transverse cuneiform bone 18, a medial cuneiform bone 20, a lateral cuneiform bone 22, a cuboid bone 24, a first metatarsal bone 26, a second metatarsal bone 28, a third metatarsal bone 30, a fourth metatarsal bone 32, a fifth metatarsal bone 34, a first proximal phalanx bone 36, a second proximal phalanx bone 38, a third proximal phalanx bone 40, a fourth proximal phalanx bone 42, a fifth proximal phalanx bone 44, a first middle phalanx bone 46, a second middle phalanx bone 48, a third middle phalanx bone 50, a fourth middle phalanx bone 52, a first distal phalanx bone 54, a second distal phalanx bone 56, a third distal phalanx bone 58, a fourth distal phalanx bone 60, and a fifth distal phalanx bone 62.

Figure 3A:
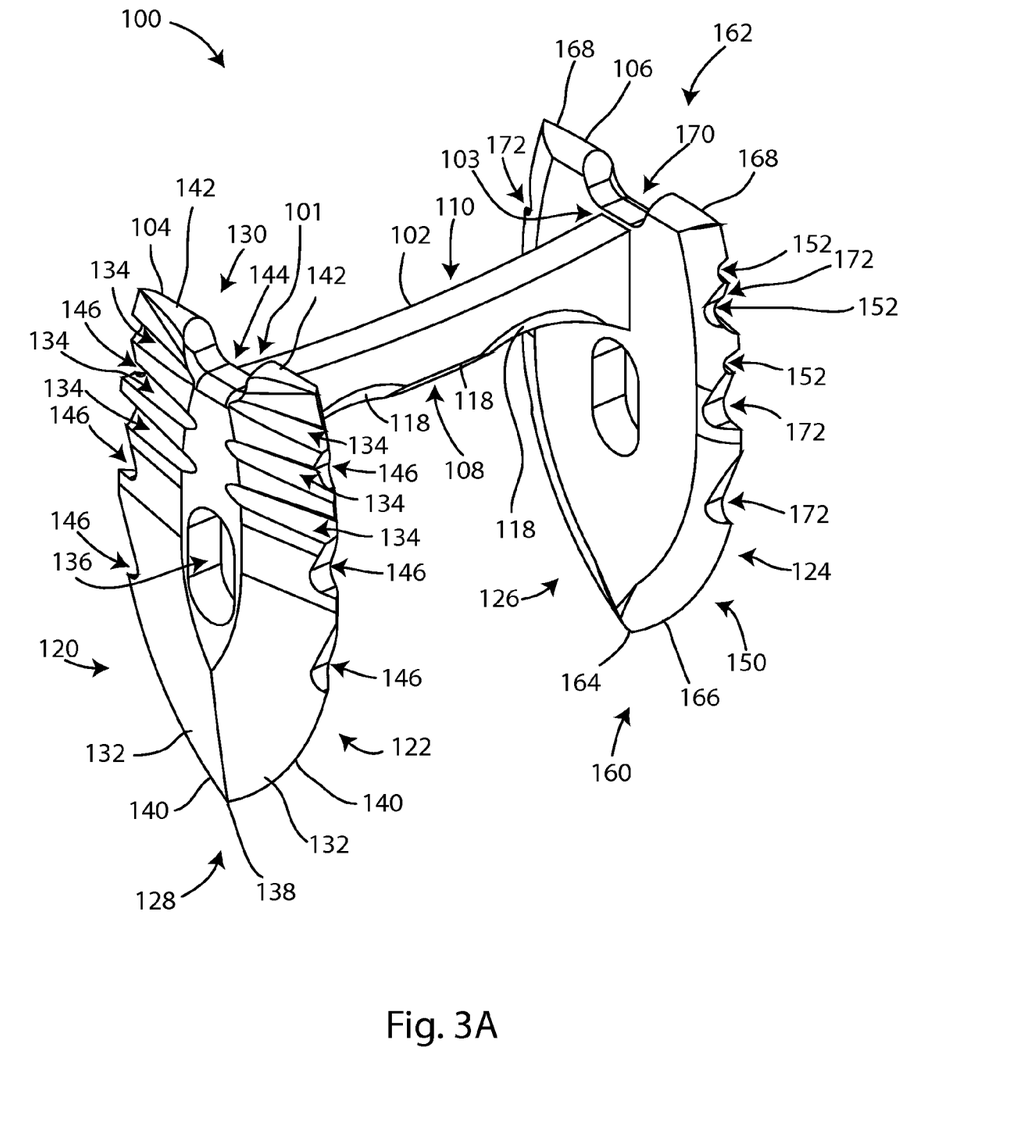
FIG. 3A is an isometric view of a device.
Figure 3B:
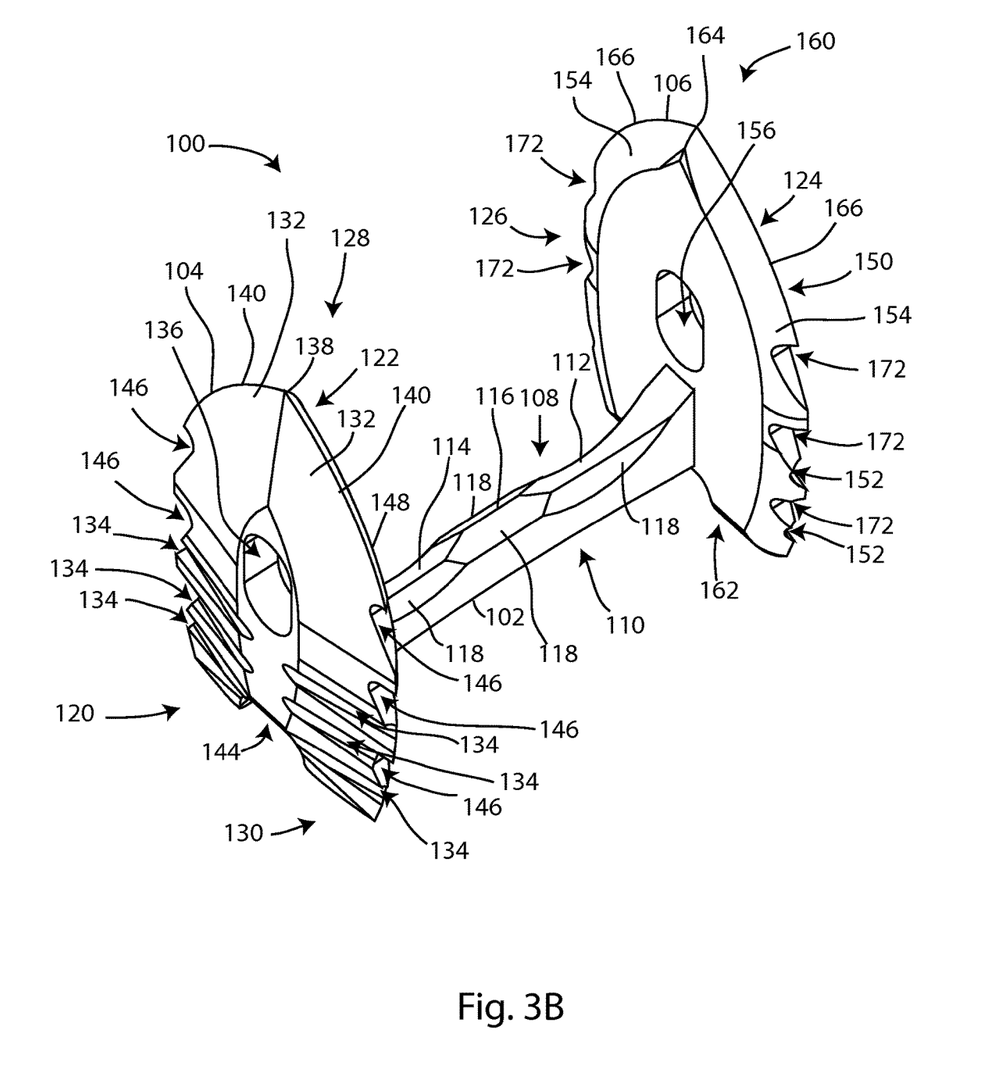
FIG. 3B is another isometric view of the device of FIG. 3A from a different angle.

Referring to FIGS. 3A-3B, a device 100 includes a central portion 102 and two lateral blades 104, 106. The blades 104, 106 extend perpendicular to the central portion 102 in the illustrated example, although other angular orientations are contemplated. For example, the blades 104, 106 may be angled to converge or diverge as the blades extend from the central portion 102.

The central portion 102 extends between a first end 101 and an opposite second end 103, and includes a leading side 108 and a trailing side 110. The leading side 108 may include blunt concave portions 112, 114. A sharpened leading edge 116 may extend at least partially across the leading side 108. In the example shown, the sharpened leading edge 116 extends across a middle region of the leading side 108. The trailing side 110 may be blunt as shown best in FIG. 3A. The central portion 102 may also include one or more beveled surfaces 118 which "break" corners that would otherwise be exterior right angle corners. In the example shown, there are six beveled surfaces 118 adjacent to the leading side 108.

The blade 104 is coupled to the first end 101 of the central portion 104 and includes an exterior surface 120 that faces away from the central portion 102 and an interior surface 122 opposite the exterior surface 120. The exterior surface 120 may include one or more sharpening surfaces 132. In the example shown, there are two broad sharpening surfaces 132. The exterior surface 120 may also include one or more grooves 134 which extend at least partially across the exterior surface 120. In the example shown, there are six grooves 134. The interior surface 122 faces toward the central portion 102. The interior surface 122 may include one or more sharpening surfaces 148. In the example shown, there are two narrow convex sharpening surfaces 148. The interior sharpening surfaces are best appreciated with reference to blade 106 which is described below. The blade 104 may also include one or more apertures 136 which extend through the blade 104 between the exterior surface 120 and the interior surface 122. In the example shown, there is a single centrally located oval aperture 136. The aperture 136 may provide an attachment point for a suture, tendon, ligament, or graft. The blade 104 may also include one or more perimeter notches 146 which extend through the blade 104 between the exterior surface 120 and the interior surface 122. The notches 146 may be described as serrations.

The blade 104 extends between a leading side 128 and a trailing side 130. The leading side 128 of the blade 104 faces in the same direction as the leading side 108 of the central portion 102. The leading side 128 of the blade 104 may include a leading point 138, and/or a sharpened leading edge 140. In the example shown, there are two sharpened leading edges 140 which meet at leading point 138. The leading edges 140 are at least partially formed by the sharpening surfaces 132, 148. The leading edges 140 may form a portion of a perimeter of the blade 106. The trailing side 130 of the blade 104 faces in the same direction as the trailing side 110 of the central portion 102. The trailing side 130 may be at least partially convex, as best seen in FIG. 3A. Bilateral convex portions 142 are illustrated in the example. The trailing side 130 may include an indentation 144, which may be centrally located.

The blade 106 is coupled to the second end 103 of the central portion 104 and includes an exterior surface 124 that faces away from the central portion 102 and an interior surface 126 opposite the exterior surface 124. The exterior surface 124 may include one or more sharpening surfaces 150. In the example shown, there are two broad sharpening surfaces 150. The exterior sharpening surfaces are best appreciated with reference to blade 104 which is described above. The exterior surface 124 may also include one or more grooves 152 which extend at least partially across the exterior surface 124. In the example shown, there are six grooves 152 like the grooves 134 of blade 104. The interior surface 126 faces toward the central portion 102. The interior surface 126 may include one or more sharpening surfaces 154. In the example shown, there are two narrow convex sharpening surfaces 154. The blade 106 may also include one or more apertures 156 which extend through the blade 106 between the exterior surface 124 and the interior surface 126. In the example shown, there is a single centrally located oval aperture 156. The aperture 156 may provide an attachment point for a suture, tendon, ligament, or graft. The blade 106 may also include one or more perimeter notches 172 which extend through the blade 106 between the exterior surface 124 and the interior surface 126. The notches 172 may be described as serrations.

The blade 106 extends between a leading side 160 and a trailing side 162. The leading side 160 of the blade 106 faces in the same direction as the leading side 108 of the central portion 102. The leading side 160 of the blade 106 may include a leading point 164, and/or a sharpened leading edge 166. In the example shown, there are two sharpened leading edges 166 which meet at leading point 164. The leading edges 166 are at least partially formed by the sharpening surfaces 150, 154. The leading edges 166 may form a portion of a perimeter of the blade 106. The trailing side 162 of the blade 106 faces in the same direction as the trailing side 110 of the central portion 102. The trailing side 162 may be at least partially convex, as best seen in FIG. 3A. Bilateral convex portions 168 are illustrated in the example. The trailing side 162 may include an indentation 170, which may be centrally located.

Figure 4:
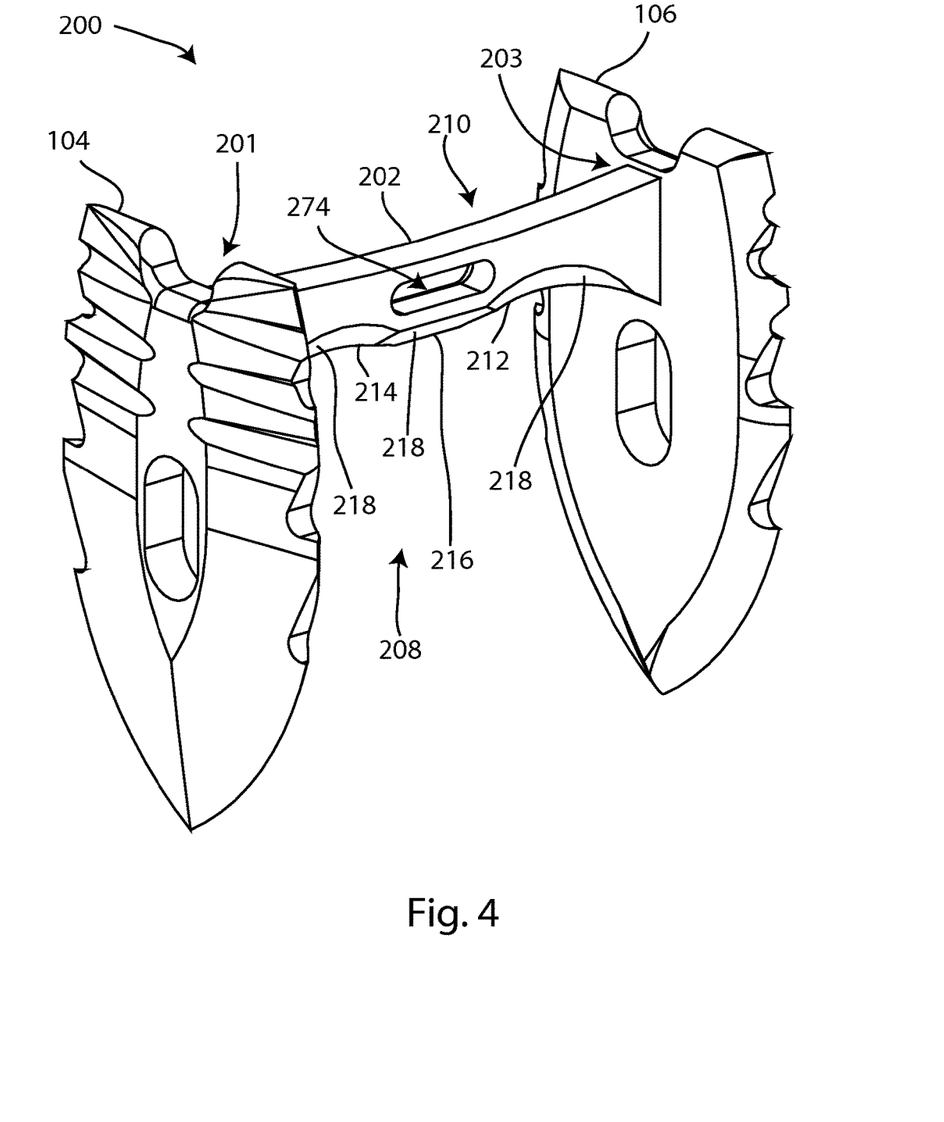
FIG. 4 is an isometric view of another device.

Referring to FIG. 4, a device 200 includes a central portion 202 and two lateral blades 104, 106. The blades 104, 106 extend perpendicular to the central portion 202 in the illustrated example, although other angular orientations are contemplated. For example, the blades 104, 106 may be angled to converge or diverge as the blades extend from the central portion 202. The blades 104, 106 in this example are identical to the blades 104, 106 of device 100.

The central portion 202 extends between a first end 201 and an opposite second end 203, and includes a leading side 208 and a trailing side 210. The leading side 208 may include blunt concave portions 212, 214. A sharpened leading edge 216 may extend at least partially across the leading side 208. In the example shown, the sharpened leading edge 216 extends across a middle region of the leading side 208. The trailing side 210 may be blunt. The central portion 202 may also include one or more beveled surfaces 218 which "break" corners that would otherwise be exterior right angle corners. In the example shown, there are six beveled surfaces 218 adjacent to the leading side 208. The central portion 202 may include one or more apertures 274 which may extend through the central portion 202 in any direction. In the illustrated example, a single centrally located oval aperture 274 extends through the central portion 202. The aperture 274 may provide an attachment point for a suture, tendon, ligament, or graft.

Figure 5A:
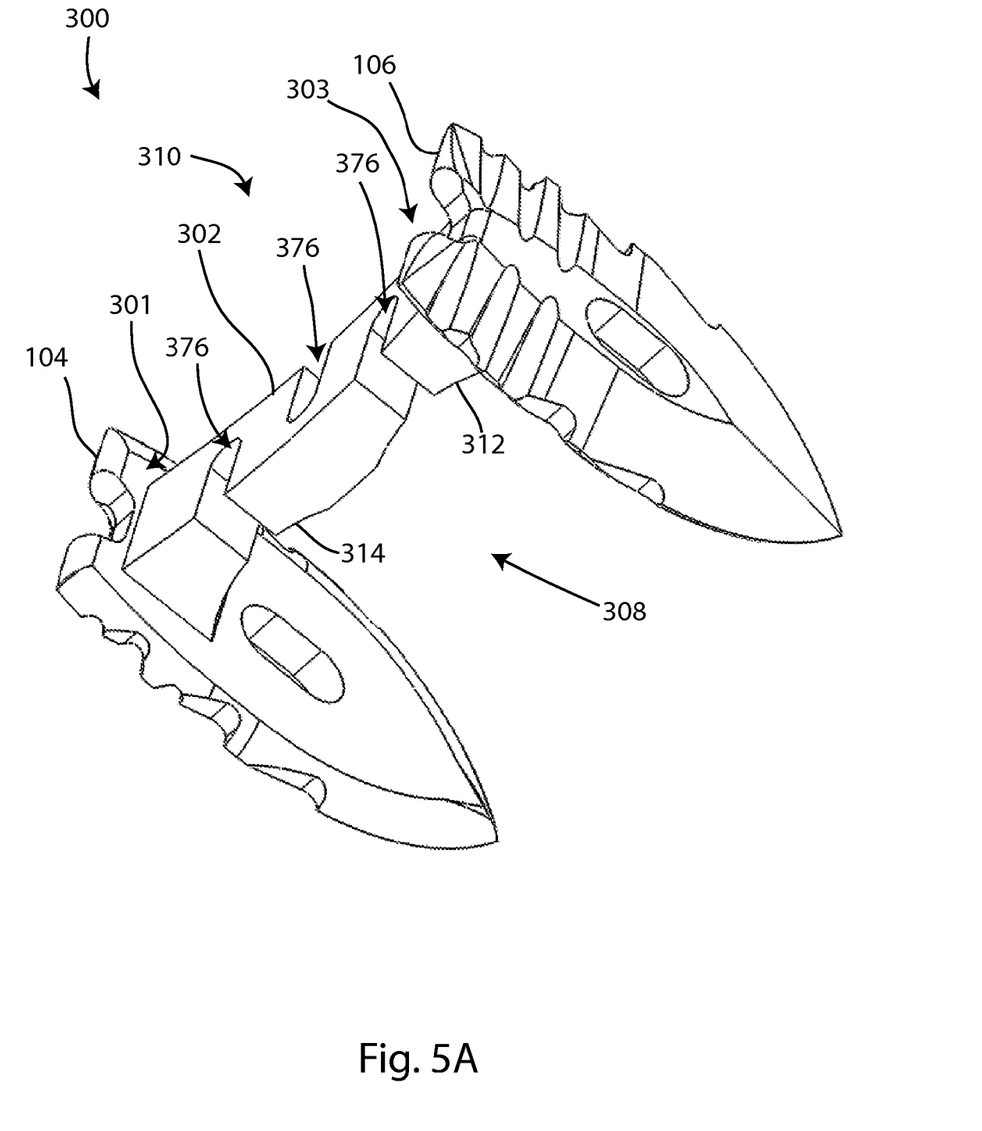
FIG. 5A is an isometric view of yet another device.
Figure 5B:
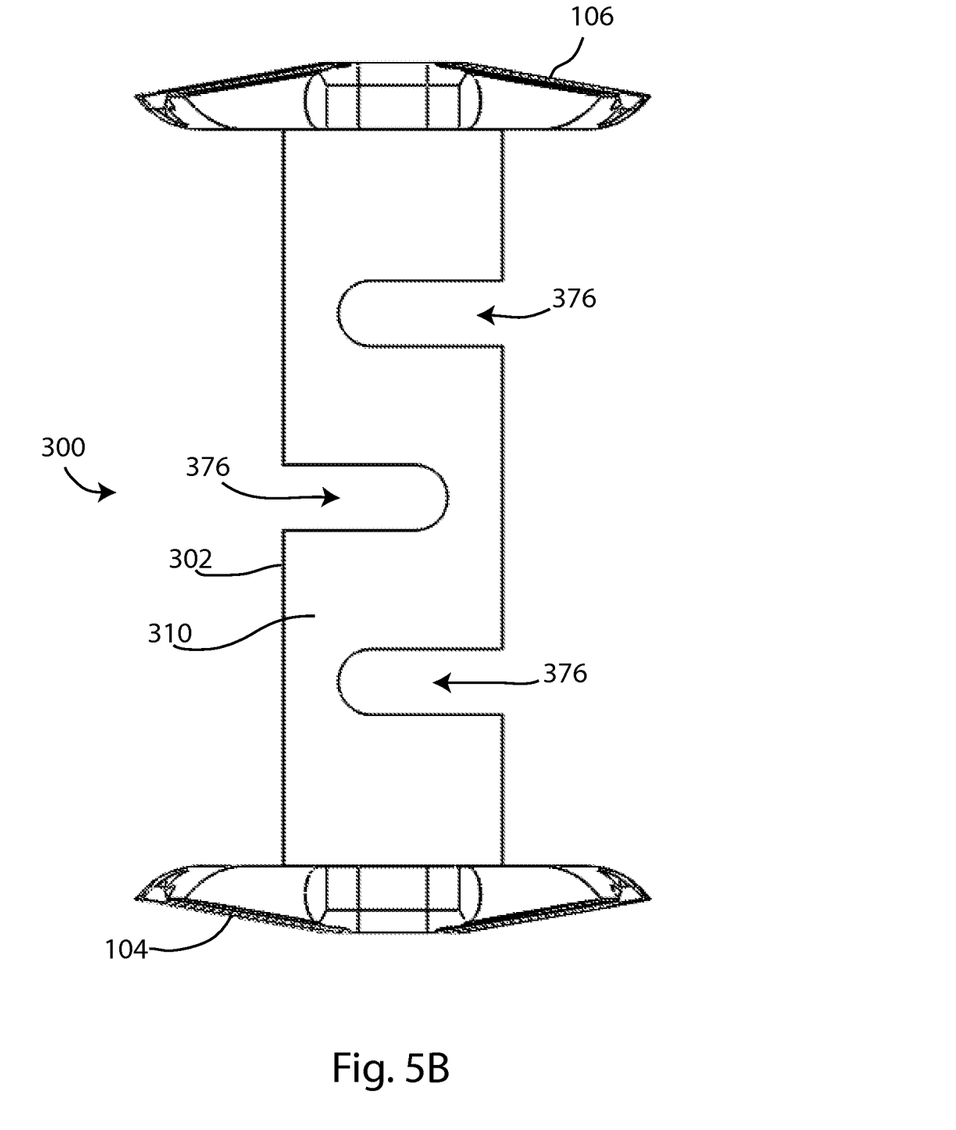
FIG. 5B is a top view of the device of FIG. 5A.

Referring to FIGS. 5A-5B, a device 300 includes a central portion 302 and two lateral blades 104, 106. The blades 104, 106 extend perpendicular to the central portion 302 in the illustrated example, although other angular orientations are contemplated. For example, the blades 104, 106 may be angled to converge or diverge as the blades extend from the central portion 302. The blades 104, 106 in this example are identical to the blades 104, 106 of device 100.

The central portion 302 extends between a first end 301 and an opposite second end 303, and includes a leading side 308 and a trailing side 310. The leading side 308 may include blunt concave portions 312, 314. The central portion 302 may also include a sharpened leading edge like edge 116 of central portion 102. The trailing side 310 may be blunt as shown best in FIG. 5A. The central portion 302 may also include one or more beveled surfaces which "break" corners that would otherwise be exterior right angle corners, like beveled surfaces 118 of central portion 102. The central portion 302 may also include one or more notches 376 which extend through the central portion 302 between the leading side 308 and the trailing side 310. In the example shown, there are three notches 376 in an alternating arrangement. This arrangement enhances the flexibility, or reduce the modulus, of the central portion 302 so that the central portion 302 may function as a spring element to provide dynamic stabilization in compression or tension in service. Central portion 302 may be described as serpentine due to the alternating notches 376. In other examples according to this principle, the central portion may include different spring elements to provide, for example, compression or tension spring behavior.

Figure 6:
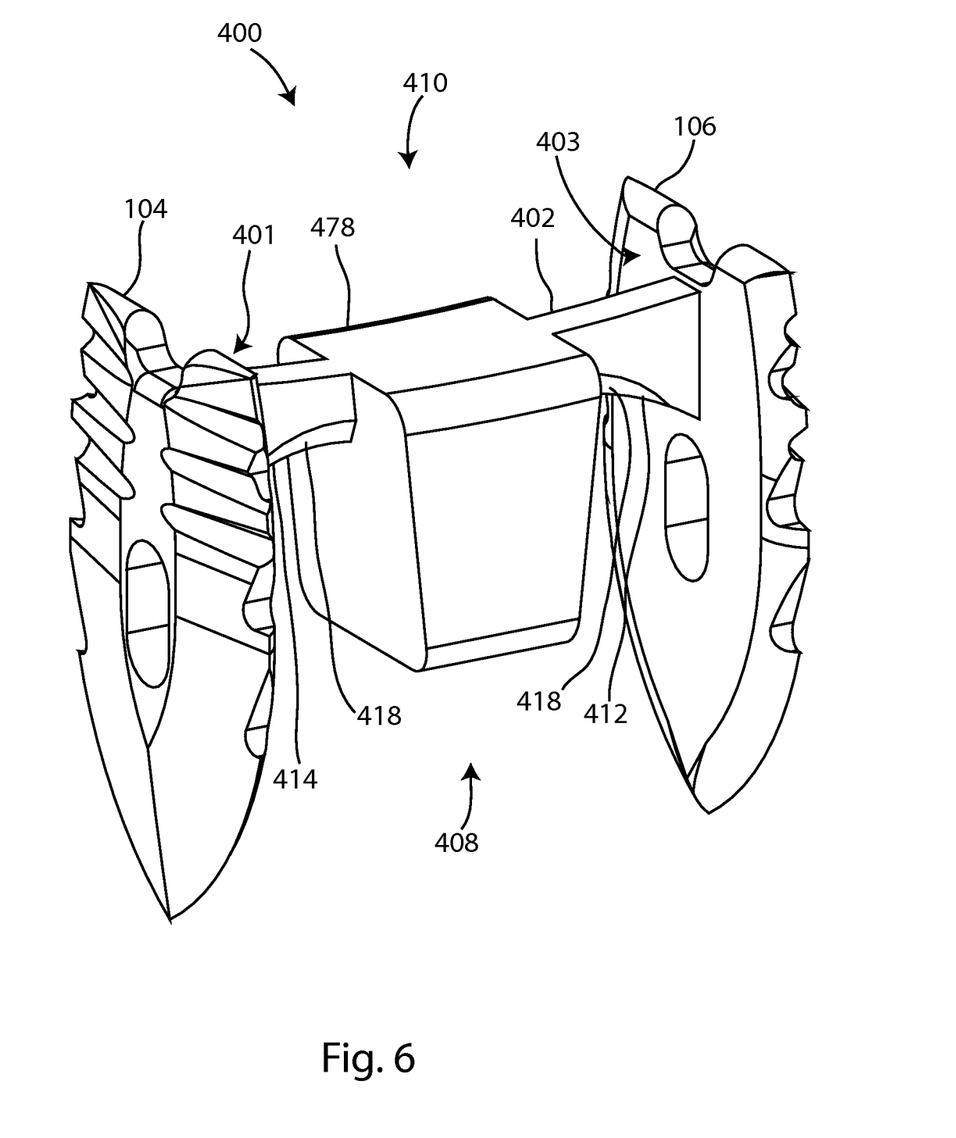
FIG. 6 is an isometric view of yet another device.

Referring to FIG. 6, a device 400 includes a central portion 402 and two lateral blades 104, 106. The blades 104, 106 extend perpendicular to the central portion 402 in the illustrated example, although other angular orientations are contemplated. For example, the blades 104, 106 may be angled to converge or diverge as the blades extend from the central portion 402. The blades 104, 106 in this example are identical to the blades 104, 106 of device 100.

The central portion 402 extends between a first end 401 and an opposite second end 403, and includes a leading side 408 and a trailing side 410. The leading side 408 may include blunt concave portions 412, 414. The trailing side 410 may be blunt. The central portion 402 may also include one or more beveled surfaces 418 which "break" corners that would otherwise be exterior right angle corners. The central portion 402 may also include one or more protrusions 478 or enlargements. The protrusion 478 may extend symmetrically or asymmetrically from the central portion 402, and may be positioned anywhere along the central portion 402. In the example shown, the protrusion 478 is centrally positioned on the central portion 402, and extends from the central portion 402 on the leading side 408 and, to a lesser degree, from adjacent sides of the central portion 402. The protrusion 478 may be a solid shape with regular or irregular planar or curved surfaces. For example, the protrusion 478 may be a polyhedron, such as a rectangular or trapezoidal solid. The protrusion 478 may be referred to as a spacer, for its function in occupying a gap between bone portions. The protrusion 478 may be made from a porous material. The protrusion 478 may be modular, and in this arrangement, may attach to the central portion 402 with a screw, a snap fit, or similar modular interconnection.

The devices disclosed herein may share at least some of the characteristics of the anchors disclosed in U.S. patent application Ser. Nos. 12/640,892; 13/666,787; and/or 13/666,956; each of which is herein incorporated by reference in its entirety.

Figure 7:
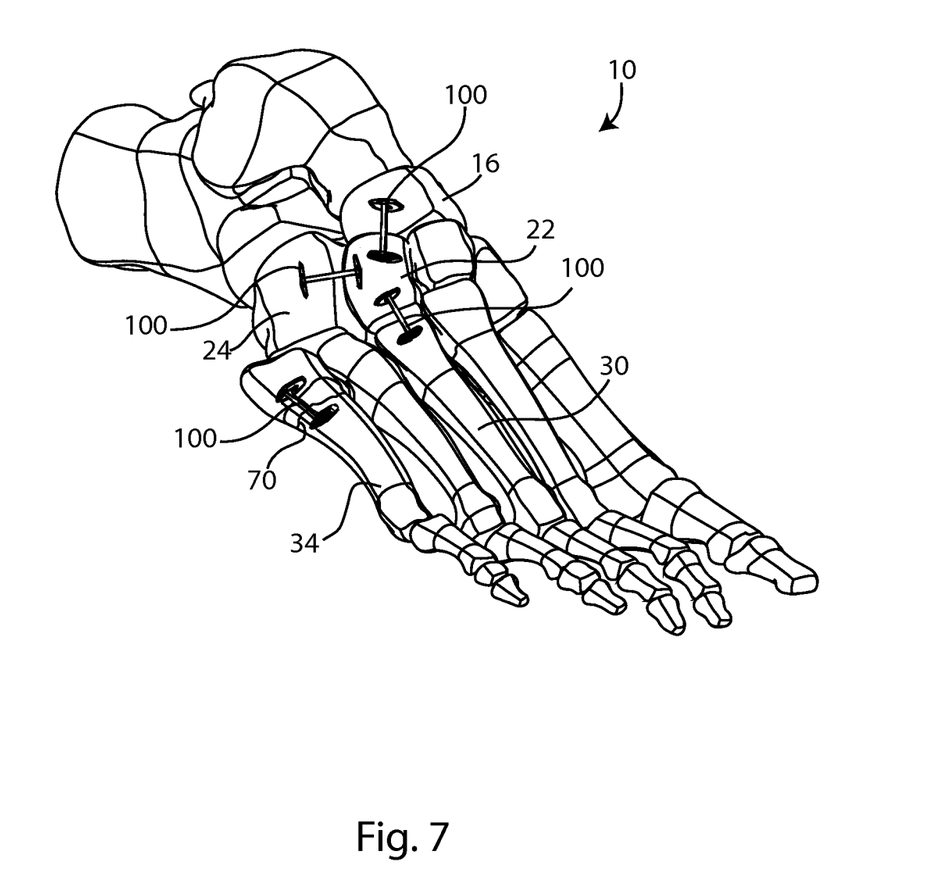
FIG. 7 is a lateral isometric view of the right foot of FIG. 1 with four of the devices of FIG. 3A implanted.

Referring to FIG. 7, the foot 10 is shown with four devices 100 implanted in various locations.

A first device 100 engages the lateral cuneiform bone 22 and the navicular bone 16. A second device 100 engages the lateral cuneiform bone 22 and the third metatarsal bone 30. A third device 100 engages the lateral cuneiform bone 22 and the cuboid bone 24. The first, second, and third devices 100 are shown in this arrangement to illustrate that any of the devices disclosed herein may engage two bones; and that a plurality of devices may engage a single bone, with each device also engaging an additional bone. The additional bones may all be different bones.

A fourth device 100 engages the fifth proximal phalanx bone 44, and may extend across a discontinuity 70 in the fifth proximal phalanx bone 44. The fourth device 100 is shown in this arrangement to illustrate that any of the devices disclosed herein may engage multiple portions of a single bone by extending across one or more discontinuities in the bone.

Figure 8:
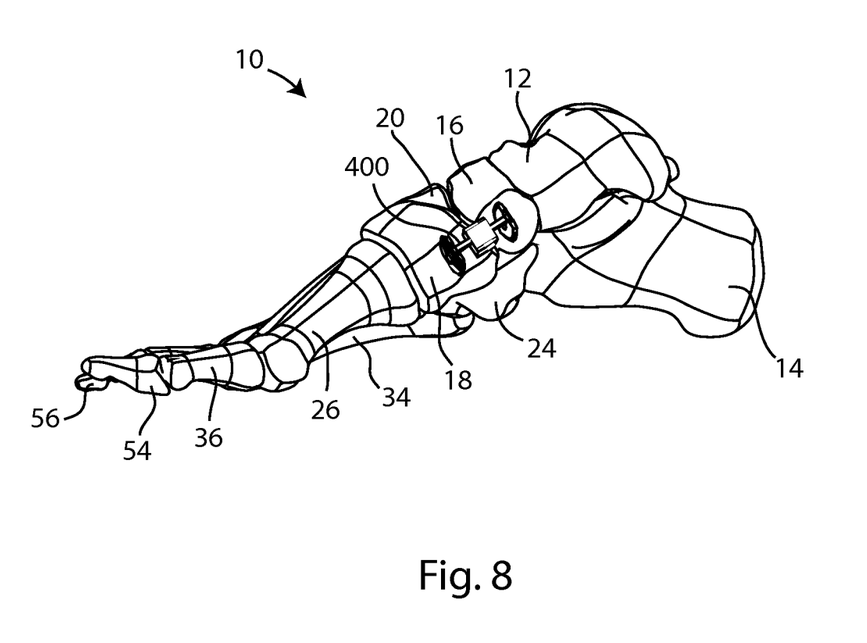
FIG. 8 is a medial isometric view of the right foot of FIG. 1 with the device of FIG. 6 implanted.

Referring to FIG. 8, the foot 10 is shown with one device 400 implanted to engage the navicular bone 16 and the transverse cuneiform bone 18. The device 400 is shown in this arrangement to illustrate that this device 400 may engage two bones. The device 400 may also engage multiple portions of a single bone by extending across one or more discontinuities in the bone.

The components disclosed herein may be fabricated from metals, alloys, polymers, plastics, ceramics, glasses, composite materials, or combinations thereof, including but not limited to: PEEK, titanium, titanium alloys, commercially pure titanium grade 2, ASTM F67, Nitinol, cobalt chrome, stainless steel, ultra high molecular weight polyethylene (UHMWPE), biocompatible materials, and biodegradable materials, among others. Different materials may be used for different parts. Coatings may be present. Different materials may be used within a single part. Any component disclosed herein may be colored, coded or otherwise marked to make it easier for a user to identify the type and size of the component, the setting, the function(s) of the component, and the like.

It should be understood that the present systems, kits, apparatuses, and methods are not intended to be limited to the particular forms disclosed. Rather, they are to cover all combinations, modifications, equivalents, and alternatives falling within the scope of the claims.

The claims are not to be interpreted as including means-plus- or step-plus-function limitations, unless such a limitation is explicitly recited in a given claim using the phrase(s) "means for" or "step for," respectively.

The term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), have (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

In the foregoing Detailed Description, various features are grouped together in several examples for the purpose of streamlining the disclosure. This method of disclosure is not to be interpreted as reflecting an intention that the examples of the invention require more features than are expressly recited in each claim. Rather, as the following claims reflect, inventive subject matter lies in less than all features of a single disclosed example. Thus, the following claims are hereby incorporated into the Detailed Description, with each claim standing on its own as a separate example.

The invention claimed is:

1. A fixation device comprising:
a central portion extending along a first direction between a first end and an opposite second end and extending along a second direction between a leading side and a trailing side, wherein the second direction is perpendicular to the first direction;
a first blade anchor coupled to the first end of the central portion; and
a second blade anchor coupled to the second end of the central portion, wherein the first and second blade anchors extend perpendicular to the central portion, wherein the first and second blade anchors each extend along the second direction between a leading side and a trailing side;
wherein the trailing sides of the first blade and second blade extend past the trailing side of the central portion along the second direction;
wherein the leading side of the central portion comprises a first blunt concave portion between the first blade anchor and a middle region of the leading side of the central portion, and a second blunt concave portion between the second blade anchor and the middle region of the leading side of the central portion, wherein the central portion comprises a sharpened leading edge that extends across the middle region of the leading side of the central portion, wherein the sharpened leading edge of the central portion is between the first and second blunt concave portions; and
wherein along the second direction, the leading and trailing sides of the central portion are between the leading and trailing sides of the first blade anchor.

2. The fixation device of claim 1, wherein the central portion comprises an aperture extending through the central portion.

3. The fixation device of claim 1, wherein the central portion comprises a spring element.

4. The fixation device of claim 3, wherein the spring element is formed by alternating notches which extend through the central portion between the leading side of the central portion and the trailing side of the central portion.

5. The fixation device of claim 1, wherein the sharpened leading edge of the central portion extends along the first direction.

6. The fixation device of claim 5, wherein the leading side of the first blade anchor comprises a sharpened leading edge, and the leading side of the second blade anchor comprises a sharpened leading edge, wherein the sharpened leading edges of the first and second blade anchors are perpendicular to the sharpened leading edge of the central portion.

7. The fixation device of claim 1, wherein along the second direction, the leading and trailing sides of the central portion are between the leading and trailing sides of the second blade anchor.

8. The fixation device of claim 7, wherein the leading side of the first blade anchor extends beyond the leading side of the central portion along the second direction; and
wherein the leading side of the second blade anchor extends beyond the leading side of the central portion along the second direction.

9. A fixation device comprising:
a central portion extending along a first direction between a first end and an opposite second end and extending along a second direction between a leading side and a trailing side, wherein the second direction is perpendicular to the first direction;
a protrusion extending from the leading side of the central portion, wherein the protrusion is a polyhedron with at least one trapezoidal side, wherein the protrusion is wider at a trailing side of the protrusion than at a leading side of the protrusion;
a first blade anchor having a leading end and a trailing end, coupled to the first end of the central portion; and
a second blade anchor having a leading end and a trailing end, coupled to the second end of the central portion, wherein the first and second blade anchors extend perpendicular to the central portion;
wherein the trailing ends of the first blade and second blade extend past the trailing side of the central portion along the second direction; and
wherein the leading side of the central portion comprises a first blunt concave portion between the first blade anchor and the protrusion, and a second blunt concave portion between the second blade anchor and the protrusion, wherein the protrusion is between the first and second blunt concave portions.

10. The fixation device of claim 9, wherein the leading end of the first blade anchor comprises a sharpened leading edge, and the leading end of the second blade anchor comprises a sharpened leading edge, wherein the sharpened leading edges of the first and second blade anchors are perpendicular to the central portion.

11. The fixation device of claim 9, wherein along the second direction, the leading and trailing sides of the central portion are between the leading and trailing ends of the first blade anchor.

12. The fixation device of claim 11, wherein the leading and trailing sides of the central portion are between the leading and trailing ends of the second blade anchor along the second direction;
wherein the leading end of the first blade anchor extends beyond the leading side of the central portion along the second direction; and
wherein the leading end of the second blade anchor extends beyond the leading side of the central portion along the second direction.

13. A fixation device comprising:
a central portion extending along a first direction between a first end and an opposite second end, extending along a second direction between a leading side and a trailing side, and extending along a third direction between a front side and a back side, wherein the first, second, and third directions are mutually perpendicular;

a first blade anchor having a leading end and a trailing end, coupled to the first end of the central portion; and a second blade anchor having a leading end and a trailing end, coupled to the second end of the central portion, wherein the first and second blade anchors extend perpendicular to the central portion, wherein the first and second blade anchors each extend outwardly from the front and back sides of the central portion along the third direction; wherein the trailing ends of the first blade and second blade extend past the trailing side of the central portion along the second direction; and wherein the leading side of the central portion comprises a first blunt concave portion between the first blade anchor and a middle region of the leading side of the central portion, and a second blunt concave portion between the second blade anchor and the middle region of the leading side of the central portion, wherein the central portion comprises a sharpened leading edge that extends across the middle region of the leading side of the central portion, wherein the sharpened leading edge of the central portion is between the first and second blunt concave portions.

14. The fixation device of claim 13, wherein the central portion comprises a spring element.

15. The fixation device of claim 14, wherein the spring element is formed by alternating notches in the front and back sides of the central portion, wherein the notches extend through the central portion between the leading and trailing sides of the central portion.

16. The fixation device of claim 13, wherein the sharpened leading edge of the central portion extends along the first direction.

17. The fixation device of claim 16, wherein the first and second blade anchors each comprise a sharpened leading edge, wherein the sharpened leading edges of the first and second blade anchors are perpendicular to the sharpened leading edge of the central portion.

* * * * *